United States Patent
Lellouche

(10) Patent No.: US 7,402,262 B2
(45) Date of Patent: Jul. 22, 2008

(54) ELECTROCONDUCTIVE POLYMERS

(75) Inventor: Jean-Paul Lellouche, Ashdod (IL)

(73) Assignee: Bar-Ilan University, Ramat-Gan (IL)

( * ) Notice: Subject to any disclaimer, the term of this patent is extended or adjusted under 35 U.S.C. 154(b) by 362 days.

(21) Appl. No.: 10/968,101

(22) Filed: Oct. 20, 2004

(65) Prior Publication Data

US 2006/0047067 A1    Mar. 2, 2006

Related U.S. Application Data

(60) Provisional application No. 60/513,559, filed on Oct. 24, 2003.

(51) Int. Cl.
*H01B 1/12* (2006.01)
*C07D 207/00* (2006.01)

(52) U.S. Cl. .................. 252/500; 548/518; 514/95; 514/183

(58) Field of Classification Search ............... 252/500; 525/54.1, 54.2; 530/815, 816; 548/400, 548/560, 562, 564, 518; 514/95, 183
See application file for complete search history.

(56) References Cited

U.S. PATENT DOCUMENTS

| 4,650,600 | A | * | 3/1987 | Heppke et al. | 252/299.01 |
| 5,837,859 | A | * | 11/1998 | Teoule et al. | 536/25.3 |
| 6,197,881 | B1 | | 3/2001 | Cosnier | |
| 6,646,106 | B1 | * | 11/2003 | Lemaire et al. | 528/398 |

OTHER PUBLICATIONS

Massart "Preparation of Aqueous Magnetic Liquids in Alkaline and Acidic Media", IEEE Transactions on Magnetics, Mag-17(2): 1247-1248, 1981. Abstract.

* cited by examiner

*Primary Examiner*—Mark Kopec

(57) ABSTRACT

Provided are novel polymerizable monomers allowing preparation of exceptionally useful surface coatings by polymerization. Embodiments include highly reticulated chiral nanoparticles useful, for example, for covalently grating biological ligands, epitaxial growth of conductive polymers onto surface modified indium tin oxide (ITO) electrodes and arrays of gold nanodots and electroconductive polymers.

39 Claims, No Drawings

ELECTROCONDUCTIVE POLYMERS

This application claims priority from U.S. Provisional patent application No. 60/513,559, filed Oct. 24, 2003, the contents of which is hereby incorporated by reference.

FIELD OF THE INVENTION

The present invention relates to the field of chemistry and particularly to novel electroconductive polymers and, respective novel monomers as well as methods for polymerizing the monomers to produce the electroconductive polymers. The present invention also relates to uses of the electroconductive polymers.

BACKGROUND OF THE INVENTION

1. Biosensors

Recently developed microfabrication techniques have facilitated the specific design and preparation of diagnostic microdevices that integrate the recognition properties of biological macromolecules with the sensitivity of electrochemical transducers. These transducers consist of conductive microsurfaces, which when modified by appropriate ligands, enable the detection and measurement of biological interactions occurring thereupon. Particularly attractive as microdevice transducers are microelectrodes covered by electropolymerized conductive polymers (ECPs) capable of immobilizing various biomolecules and ligands such as enzymes, proteins, antibodies and small ligands (for example, catalysts, porphyrins, DNA/cDNA/RNA sequences and the like). ECPs are infusible and insoluble organic materials which show intrinsic electronic conductivities due to their highly conjugated backbones.

The main advantages of ECPs are (1) a capacity to be mildly electrogenerated on microelectrodes of defined geometries, (2) electroconductivity, allowing strictly controlled growth of the polymeric layers, (3) the relative ease of chemically modifying the electropolymerizable precursor monomers, and (4) the known compatibility of the oxidative/reductive electrochemical conditions with peptides and DNA sequences for film generation onto electrodes.

Basically, in order to build biosensing microdevices successfully, two main strategies can be envisaged for stable immobilization of any biomolecule or ligand onto an electrode via ECPs: entrapment within a growing polymer during the respective electrochemical growth process or covalent attachment onto a preformed functionalized polymer. In the case of proteins and for some smaller ligands, the former strategy is plagued by a number of problems: difficult access of analytes to the immobilized proteins and reduced activities of entrapped enzymes. Additionally, it should be noted that the direct grafting of precursor monomer-linked biological macromolecules does not provide homopolymerization although an electrochemical copolymerization process with unsubstituted monomers can afford the desired biopolymers. Consequently, much of the effort to develop ECPs as matrices for the covalent grafting of various biomolecules or ligands (e.g., proteins, antibodies) in the biosensor field has been directed towards the search for polymers with improved performance chemically activated surfaces. For example, useful precursor polymers have been produced by polymerizing specially functionalized racemic thiophene or pyrrole monomers onto metallic microelectrodes. Additionally, the great versatility of ECPs find a novel and exciting application in the newly emerging field of biochip technologies and related surface modifications.

2. The Biochip Field

Shifting from single analyte tests (biosensors) to integrated assemblies, or arrays of molecular probes allowing for massive parallel throughput screening, has fueled the active development of ligands or molecular probes matrices (biochips) functionalized by diverse DNA, cDNA, peptides or proteins entities. Highly parallel screening of suitable analytes at a high density and capacity format are the main characteristics of biochips technologies. But, functionalizing a given support surface as a bidimensional matrix of molecular probes without cross-contamination requires, developing a versatile surface chemistry able to selectively link these molecular probes onto the support, preferably covalently for analytical reliability. Different kinds of surface chemistries have been designed and developed in this field owing (1) to diagnostic applications, (2) to desired surface densities of molecular probes, (3) to their chemical types, as well as (4) to detection methods for fingerprint analysis after analyte incubation (using, for example, radioactivity, fluorescence, luminescence, electroluminescence and electrochemical techniques). For example, the Affymetrix (Santa Clara, Calif., U.S.A) method consists of arrays of target DNA sequences synthesized combinatorially on aminated silicon wafers, using protected photosensitive N-acyl-deoxynucleoside phosphoramidites, for the consecutive elongation of the oligodeoxynucleotide probes on the chip surface. High density DNA biochips have been produced (400,000 DNA probes) onto a 1.28 cm$^2$ silicon surface. Moreover, the APEX silicon chip of Nanogen (San Diego, Calif., U.S.A.) contains an array of 64 micro-electrodes, each with a different DNA segment attached via an aminated or streptavidin permeation polymeric layer. Electric currents are used to direct the oligodeoxynucleotide probes onto the activated electrodes with a concomitant increase in the rapidity of the hybridization reaction.

Regarding the use of ECPs, another method makes use of functional DNA-linked ECPs on a chip bearing 128 microelectrodes (CisBio International, Bagnols-sur-Ceze, France). The microelectrodes are sequentially functionalized by oxidative electropolymerization of oligodeoxynucleotide-pyrrole probes. Those chips have been used for genetic testing and pathogen identification based on DNA sequences probes.

In the same trend of research and mainly driven by cost and technical simplicity, the present inventor and associates have developed a novel and general concept for the production of DNA/cDNA/RNA/proteins biochips which use biotinylated surfaces and the well-known avidin-biotin system for quasi-covalent probe attachment onto the biochips surfaces ($K_d=10^{-15}$). This substrate-protein interaction is always viewed as an extraordinary tool for bioconjugation in molecular biology and numerous reagents have been chemically modified by biotin for diagnostic purposes like immunological systems. Interestingly, this approach to diagnostic biochips integrates surface modifications by a sublayer of biotinylated-poly(dipyrrole) ECPs with the use of commercially available micro/nanospotting devices for surface arraying to produce the required matrices of probes.

3. Functional ECPs

U.S. Pat. No. 6,197,881 describes electrically conductive copolymers suitable for presenting a wide variety of biologically interesting molecules on a surface, especially in a surface array or matrix useful in the preparation of biochips and biosensors. More specifically, there is taught a conductive copolymer consisting of two oxidizable and polymerizable monomers "A" and "B". A is a first polymerizable monomer containing a biotin (or a complex of biotin) as a functional group and it produces an electrically conductive polymer when polymerized. B is a second polymerizable monomer, lacks the biotin functional group, but may contain a group having a desired chemical functionality, which when copolymerized with monomer, or polymer A produces an electrically conductive copolymer. A and B are independently selected from the group consisiting of pyrrole, carbazole, acetylene, azine, p-phenylene, p-phenylene vinylene, pyrene, thiophene, furan, selenophene, pyridazine, aniline and tyramide.

The oxidizable pyrrole moiety of the A and B monomers described in U.S. Pat. No. 6,197,881 form, after oxidation, long polymeric chains (see below the indicated polymer growth directions). The resulting copolymer films exhibit a highly cross-linked skeleton and, hence, the mechanical stability and ionic permeability essential for polymer growth.

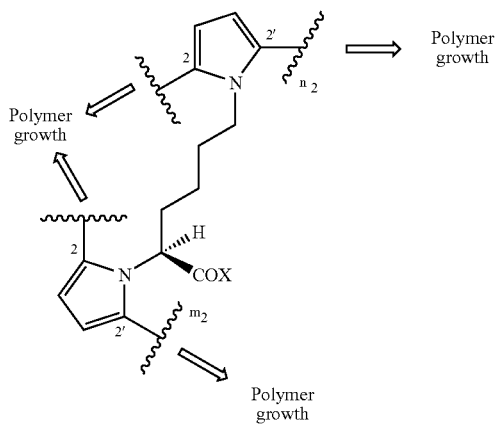

wherein X represents OH, —HN—$(CH_2)_n$—$NH_2$ or —HN—$(CH_2)_n$—NH-biotin; n represents an integer equal or greater than 1; and $n_2$ and $m_2$ indicate the degree of polymerization of the drawn polymer and are such that averaged molecular weights of more than 1,000,000 Daltons are routinely obtained.

The proximity of an electron withdrawing ester group to one of the two oxidizable groups should differentiate them oxidatively, and enable us to modulate the structural and physico-chemical properties of resulting films.

More specifically, the conductive copolymer of the U.S. Pat. No. 6,197,881 is formed by electropolymerization of two co-monomers, only one of them containing a functional group capable of binding a ligand, having the general structure:

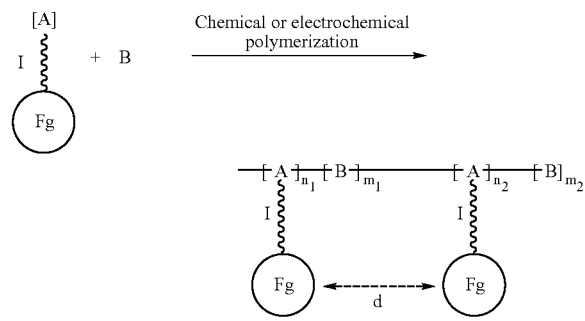

A and B are oxidizable moeities (pyrrole; carbazole, thiophene and the like), A is chemically functionalized whereas B is not functionalized. A and B can represent identical or non-identical moieties Fg is a functional group capable of binding a ligand and it is linked to the oxidizable moiety A. It is biotin (or a biotin-containing complex) in the monomers described in the U.S. Pat. No. 6,197,881;

The linker separates the oxidizable moeity A from the functional group Fg. The linker can be of any chemical nature;

n1, m1, n2 and m2 represent the number of the individual monomers in the copolymer and they may be identical, or non-identical;

d is the average distance between two Fg groups linked to oxidized A units in the copolymeric chain. This distance is absolutely not homogenous in the case of co-polymers.

U.S. Pat. No. 6,197,881 provides some preliminary data on biochip preparation using biotinylated ECPs.

There are some major disadvantages characterizing the polymers of the U.S. Pat. No. 6,197,881:

1. The copolymerized product described in U.S. Pat. No. 6,197,881 contains functional groups in a non-organized arrangement in which the distance between adjacent functional groups, each capable of binding a ligand, is irregular and sporadic.

2. Of the two electropolymerizable monomers participating in the formation of the copolymer of U.S. Pat. No. 6,197, 881, only one contains a functional binding group (biotin). The functional groups (biotin) of such copolymer have the limitation of sporadically spreading over the biochip surface. Consequently, it is neither possible to plan the desired distance between two adjacent active combining groups nor it possible to surface engineer tailor-made nanoscale assemblies in which the distance between the adjacent active binding groups is pre-determined in rational way.

3. Neither of the monomers described in U.S. Pat. No. 6,197,881 contains optical active chiral center. Consequently, the polymer layers lack the stereoselectivity frequently required for specific binding of a ligand.

In light of the above, it is clear that there is a need for a new polymerized conductive polymer (ECP) for surface engineering of novel nanoscaled assemblies. These assemblies are useful in a wide scope of biological applications relying mainly on the covalent grafting of specific ligands (such as, for example, proteins; DNA/cDNA/RNA sequences) to active binding groups exist on spherical, hemispherical or planar polymeric surfaces structures at A nanoscale level.

More specifically, there is a need for:

(a) a C2-C6 fully symmetrical polymerizable monomer containing at least two identical oxidizable groups and at least two chiral centers, wherein each of the chiral carbon atom links a carboxylated group capable of binding a functional group or a ligand; and (b) a polymerizable monomer containing at least two non-identical oxidizable groups and at least two chiral centers, wherein each of the chiral carbon atoms links a carboxylated group capable of binding a functional group or a ligand.

Such a group of monomers is henceforth referred to as C2-C6 "pseudo-symmetrical" monomers.

There is also a need for C2, C3, C4, C5, and C6 symmetrical and pseudo-symmetrical monomers, as described above, wherein during the (co)polymerization process the oxidizable groups are subjected to diverse electrochemical and chemical oxidation/reduction techniques.

There is also a need for polymeric chiral-linked functional groups (ECP) adsorbed on microelectrodes that can be used for the covalent grafting of biological ligands such as proteins, enzymes; antibodies amino-linked DNA/cDNA/RNA.

There is also a need for an array of biosensors of nanoscaled electrodes capable of chirally matched-mismatched grafting of chiral biological probes onto chiral polymeric films.

There is also a need for highly reticulated polymeric (ECP)-, and/or composite polymeric (ECP)-magnetic nanoparticles for covalently grafting various biological probes.

There is also a need for the epitaxial growth of chiral monomers onto oxidizable siloxane-based monolayers as a novel way to engineer conductive surfaces.

There is also a need for array of composite gold-carboxylated polymeric ECPs nanoelectrodes.

There is also a need for a nanoscaled chiral polymeric (ECP) cylinder capable of covalently grafting of amino-containing biological probes.

There is also a need for biosensor and/or biochip devices comprising nanoscaled chiral polymers (ECP) capable of covalently grafting amino-containing biological probes.

SUMMARY OF INVENTION

Embodiments of the present invention successfully address at least some of the shortcomings of the prior art.

Specifically, embodiments of the present invention provide:

(a) a C2-C6 fully symmetrical polymerizable monomer containing at least two identical oxidizable groups and at least two chiral centers, wherein each of the chiral carbon atoms links a carboxylated group capable of binding a functional group or a ligand; and (b) a polymerizable monomer containing at least two non-identical oxidizable groups and at least two chiral centers, wherein each of the chiral carbon atoms links a carboxylated group capable of binding a functional group or a ligand.

Such a group of monomers is henceforth referred to as C2-C6 "pseudo-symmetrical" monomers.

Embodiments of the present invention include C2, C3, C4, C5, and C6 symmetrical and pseudo-symmetrical monomers, as described in above, wherein during the (co)polymerization process the oxidizable groups are subjected to diverse electrochemical and chemical oxidation/reduction techniques.

Embodiments of the present invention provide polymeric chiral-linked functional groups (ECP) adsorbed on microelectrodes useful for covalent grafting of ligands, including but not limited to proteins, enzymes, antibodies amino-linked DNA/cDNA/RNA.

In an embodiments of the present invention there is provided an array of biosensors of nanoscaled electrodes configured to allow chirally matched-mismatched grafting of chiral biological probes onto chiral polymeric films.

Embodiments of the present invention include highly reticulated polymeric (ECP)-, and/or composite polymeric (ECP)-magnetic nanoparticles suitable for covalently grafting various biological probes.

Embodiments of the present invention include epitaxial growth of chiral monomers onto oxidizable siloxane-based monolayers, useful for rationally designing conductive surfaces.

Embodiments of the present invention provide an array of composite gold-carboxylated polymeric ECPs nanoelectrodes.

Embodiments of the present invention provide nanoscale chiral polymeric (ECP) cylinder configured for the covalent grafting of amino-containing biological probes.

Embodiments of the present invention are of biosensors and/or biochip devices comprising nanoscaled chiral polymers (ECP) configured for the covalent grafting of amine-containing biological probes.

In an embodiment of the present invention, provided is an optical active monomer containing at least two oxidizable groups and at least two chiral centers of the general formula:

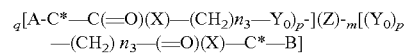

wherein, —C(=O)X represents an activated carboxyl group capable of binding a functional group or a ligand; wherein such binding may occur pre- or post-(co)polymerization process, and when —C(=O)(X) represents a free carboxylic group also a salt of such a free carboxylic group;

X represents a moiety of a molecule capable of reacting with a nucleophile group; A and B may be the same or different, and each represents an oxidizable group; when A and B are not identical, the monomer is referred to as "pseudo-symmetric monomer";

Z represents a two- to six-valence center, core (or nucleus) of the C2-C6 symmetric or pseudo-symetric monomer;

$Y_0$ represents a divalent radical which links the center of the C2-C6 symmetric or pseudo-symmetric monomer to the —$(CH_2)n_3$ chain;

p is an integer selected from 0 or 1;

$n_3$ is an integer from 0-100;

q and m each represents an integer from 1-5; provided that the sum of q+m is an integer from 2 to 6;

$Y_1$ represents the group —$(Y_0)_p$-(Z)-$(Y_0)_p$—

An embodiment of the present invention is directed towards obtaining optical active monomers containing at least two stereoselective center. An embodiment of the present invention is directed towards providing (co)polymers containing Fg groups organized in a desired arrangement, in which the distance between two adjacent Fg groups are both controllable and predetermined.

Surprisingly it is found that using a polymerizable monomer containing at least two identical, or non-identical oxidizable groups and at least two chiral centers, wherein each of the chiral carbon atoms links a functional group capable of binding a ligand, provides, upon (co)polymerization, tailor-made nanoscale (co)polymeric assemblies in which any desired distance between adjacent functional ligand combining groups is, if desired, designed, planned, predetermined and controlled.

Thus, an embodiment of the present invention is of novel monomers of the present invention containing:

(a) at least two chiral carbon atoms, wherein each of said chiral carbon atoms links a functional group, capable of binding a ligand; and (b) at least two oxidizable groups suitable for providing a conductive (co)polymer.

The (co)polymerization of the monomers of present invention provides (co)polymers with a pre-determined, controllable, well defined distances ($d_1$ and $d_2$) between two adjacent functional groups.

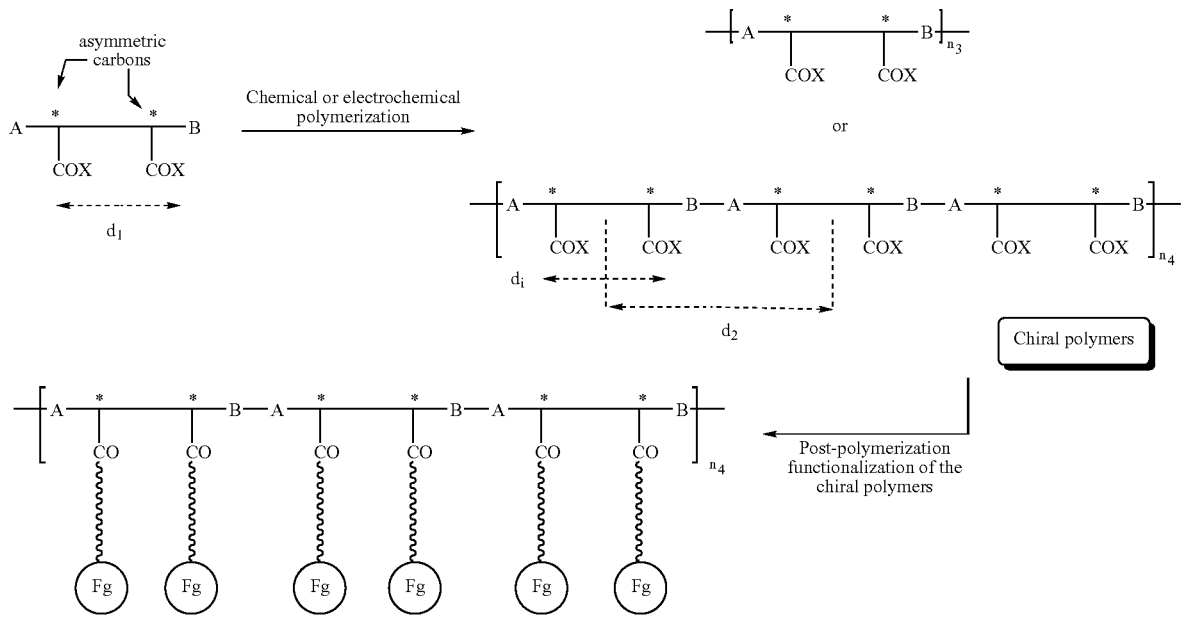

wherein,

A and B are oxidizable moeities (including but not limited to pyrrole, carbazole, thiophene and the like);

$d_1$ represents the fixed distance between two adjacent functional groups on the same monomer, whereas $d_2$ represents the distance between two adjacent functional groups, each located on a different monomer. In embodiments of the present invention, either or both $d_1$ and, $d_2$ are rationally predetermined and are controllable, preferably by the proper choice and design (as disclosed herein) of a respective monomer. Such controllable arrangement of the active functional binding groups confers specific surface properties to the produced polymers. In embodiments of the present invention, monomers of this type (i.e., having at least two chiral active binding groups per monomer) are combinatorially-mixed so as to produce a large array of diverse polymers in which the distance between inter functional binding groups is "averaged" to provide optimized parameters of the given polymeric surface (e.g., porosity, ionic permeability, conductivity, roughness and reticulation, density of functional groups, surface charges, surface ratio lipophilicity/hydrophobicity, averaged diameters of the polymeric matrices, and sintering effects of the same matrices).

The sign * represents an active optical center derived from the at least two chiral carbon atoms on each monomer. Each assymetric carbon links an activated carboxyl group. Consequently, stereoselective recognition of chiral aminated macromolecules or amino-modified probes may induce different permeation rates through the polymeric films resulting in matrices capable of chiral discrimination. As an example, the density of amino-coupling carboxylates as well as their position inside the polymeric films could be affected and could directly influence enzymatic reactions occurring at this chiral solid-liquid interface via "matched-mismatched" interactions with chiral macromolecules or even smaller biological ligands.

Fg represents a functional group that may be linked to the activated carboxyl group of the individual monomer either in a pre-polymerization process or in a post-(co)polymerization process. The activated carboxyl groups confer to the polymers the capability of being structurally modified with virtually any existing chemical functionality providing through use of amino-linked Fg bifunctional linkers. Furthermore, the monomers or (co)polymers of the present invention have the capability of chiral discrimination for amino-containing chiral macromolecules (protein, DNA sequences, and the like).

DESCRIPTION OF EMBODIMENTS OF THE INVENTION

An embodiment of the present invention is a polymerizable monomer containing at least two oxidizable groups and at least two chiral centers, wherein each of the chiral carbon links a functional group that is capable of binding a ligand. (Co)polymerization of such monomers yields (co)polymers having controllable, organized arrangement of said functional groups on the surface of the (co)polymer.

The principles and uses of the teachings of the present invention may be better understood with reference to the accompanying description and examples.

Before explaining at least one embodiment of the invention in detail, it is to be understood that the invention is not limited in its application to the details set forth herein. The invention can be implemented with other embodiments and can be practiced or carried out in various ways. It is also understood that the phraseology and terminology employed herein is for descriptive purpose and should not be regarded as limiting.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents and, other references mentioned herein are incorporated by reference in their entirety. In case of conflict, the patent specification, including definitions, will control. In addition, the materials, methods, and examples are illustrative only and not intended to be limiting.

The terms "comprising" and "including" or grammatical variants thereof when used herein are to be taken as specifying the stated features, integers, steps or components but do not preclude the addition of one or more additional features, integers, steps, components or groups thereof. This term encompasses the terms "consisting of" and "consisting essentially of".

The phrase "consisting essentially of" means that the composition may include additional ingredients, but only if the additional ingredients do not materially alter the basic and novel characteristics of the claimed compositions or methods.

The term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

In an embodiment of the present invention, a polymerizable monomer of the present invention ahs the general formula:

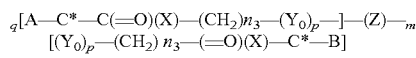

wherein,

—C(=O)X represents an activated carboxyl group capable of binding a functional group or a ligand; wherein such binding may occur pre- or post-(co)polymerization process, and when —C(=O)(X) represents a free carboxylic group also a salt of such a free carboxylic group;

X represents a moiety of a molecule capable of reacting with a nucleophile group. Suitable X moieties include but are not limited to —$OR_3$ or $SR_3$ groups, in which $R_3$ represents hydrogen, an organic group, such as optionally substituted aliphatic, cyclic, aromatic or heterocyclic group or any combination thereof, metal or any other positive ion. Additionally suitable X moieties include but are not limited to —$NR^1R^2$ wherein $R^1$ and $R^2$ each represents H or an organic group; —N-succinimide, —N-phthalimide, pentafluorophenyl (see Scheme 1), biotin, aromatics, sugars or 1,2-/1,3-amino alcohols;

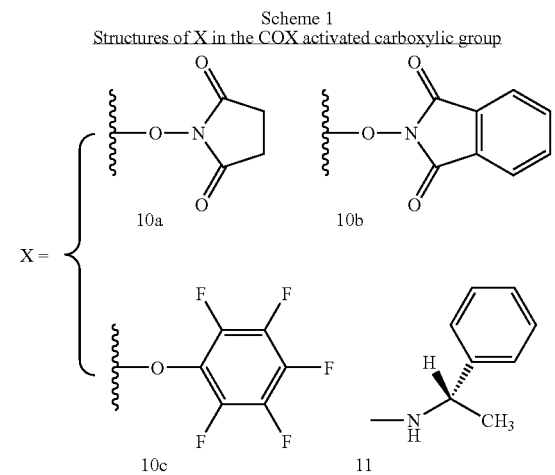

Scheme 1
Structures of X in the COX activated carboxylic group

A and B may be the same or different oxidizable group. Suitable A or B groups include but are not limited to pyyrole, dicarbazole, acetylene, azine, p-phenylene, p-phenylene-vinylene, pyrene, thiophene, furan, selenophene, pyridazine, aniline and tyramide; when A and B are not identical, the monomer is referred to as "pseudo-symmetric monomer";

Z represents a two- to six-valence center, core (or nucleus) of the C2-C6 symmetric or pseudo-symetric monomer. Suitable Z centers include but are not limited to single atoms, such as, for example, C, N, S. Se, Si, O and P. Suitable Z centers include but are not limited to groups of atoms, such as, for example, —O—Si($R_1$)($R_2$)—O—; —O—Si(—O—)(—O—)—O—; —O—Si(—O—)($R_1$)—O—; CO; $CH_2$; CH; HNCO; HNCONH; NCON; —S—S— linear or branched hydrocarbon chain; cyclo-hydrocarbon, aromatic and heterocyclic rings; $R_1$ and $R_2$ are the same or different and each represents a monovalent radical;

$Y_0$ represents a divalent radical which links the center of the C2-C6 symmetric or pseudo-symmetric monomer to the $(CH_2)n_3$ chain. Suitable $Y_0$ divalent radicals include but are not limited to, an optionally substituted linear or branched alkylene ($C_1$-$C_{30}$) and optionally substituted arylene or alkarylene or aralkylene;

$Y_1$ represents the group —$(Y_0)_p$-(Z)-$(Y_0)_p$—. Suitable $Y_1$ groups include but are not limited to, the groups HNCONH; —NHCO—$(CH_2)$t-CONH—, —CONH—$(CH_2)_t$—NHCO— wherein t represents an integer from 1 to 20;

p is an integer selected from 0 or 1;

$n_3$ is an integer from 0-100;

q and m each represents an integer from 1-5 where the sum of q+m is an integer from 2 to 6.

The monomers of the present invention are used for producing the nanoscaled assemblies of present invention and for engineering surfaces tailored for biotechnological applications (e.g., grafting of biological ligands). Furthermore, they are used for synthesizing combinatorially engineered polymers of the same type for nanoscale engineering of conductive planar and non-conductive spherical surfaces.

Three preferred embodiments of uses of the oxidizable symmetric monomers of the present invention that are discussed in detail herein are: (A) providing highly reticulated chiral nanoparticles (paramagnetic or not) capable of covalently grafting various ligands, especially biological ligands (B) providing epitaxial growth of related ECPs on a conductive surface, such as, an electrode, and (C) use in two-dimensionally structured gold nanodot planar arrays and in siloxane-based self-assembled monolayers.

A. Preparation of Highly Reticulated Chiral Nanoparticles and their Surface Modifications for Covalent Grafting of Biological Ligands We have used the carboxylated-dipyrrole, dicarbazole and pyrrole-carbazole monomers LL-22 to DD-51 of the indicated formula (Schemes 2, 2a and 2b: $Y_1$ and $n_3$ similarly defined for the whole set of structures) for the preparation of highly-reticulated carboxylated poly(dipyrrole), poly(dicarbazole) and poly(pyrrole-carbazole) nanoparticles and magnetically responsive $Fe_3O_4$-poly(dipyrrole), -poly(dicarbazole) and -poly(pyrrole-carbazole) nanocomposite particles 52-53 (Scheme 3) for covalent grafting of biological ligands, such as, for example, proteins, antibodies and amino-linked DNA/RNA sequences. Besides these monomers, additional novel carboxylated-dipyrrole and dicarbazole monomers of C2-symmetry but absolute DD configurations DD-32 to DD-41 (Scheme 2a) and hybrid pyrrole-carbazole of the LL or DD absolute configurations of LL-42/LL-46 to the corresponding DD-47/DD-51 monomers (Scheme 2b) were used. The same is true regarding the conversion from the DD structures DD-42/DD-46 to the corresponding LL configurations LL-47/LL-51. Of course monomers consisting of DL or LD configurations are applicable, as well. In other words, due to C2-symmetry and two chirality centers in the monomers of the present invention, starting from L-amino acids, would provide L,L-compounds and, starting from the optically inverse D amino acid, would provide the D,D monomers.

This innovative highly reticulated chiral nanoparticles design allows the study of the effects of various structural parameters such as monomer chirality, length and type of the group $Y_1$, mode of reticulation and types of oxidizable heterocycles. This allows optimization of the the covalent attachment of biological ligands and at the same time increases the options for obtaining nanoparticles which are adapted to a targeted biological application.

From the synthetic point of view, commercially available and orthogonally protected amino acids derived from L- or D-serine, L- or D-lysine and L- or D-aspartic/glutamic acids are suitable starting compounds. Pyrrole or carbazole units are introduced using a modified Clauson-Kaas reaction resulting in the intermediates 14-21 (Scheme 2). Simple amide coupling chemistry using α,ω-diacids or diamines (dicyclohexyl carbodiimide (DCC), hydroxybenzotriazole (HOBt), anhydrous dimethylformamide (DMF) or dialkyl/diphenyl dichlorosilanes (Hanessian's conditions: anhydrous DMF, imidazole (Im)) or phosgene (15% toluene solution, anhydrous $CH_2Cl_2$, diisopropylethylamine (DIPEA), room temperature (RT)) followed by basic saponification affording the desired C2-symmetrical or hybrid precursor monomers for nanoparticle and functional film preparation. Post-synthesis optical purities can be determined by NMR analysis (when for the example has C2-symmetry) and/or derivatization to chromatographically distinguishable diasteromers followed by assay using, for example HPLC. The preparation of magnetically responsive nanocomposite particles is, for example, made in the presence of magnetite. Oxidizing agents include but are not limited to $FeCl_3 \cdot 6H_2O$, $K_2S_2O_8$ or $H_2O_2$/catalytic $FeCl_3$/traces example, aqueous or aqueous-organic solvent media.

SCHEME 2

C2-Symmetrical dipyrrole, dicarbazole and pseudo-symmetrical pyrrole-carbazole oxidizable monomers

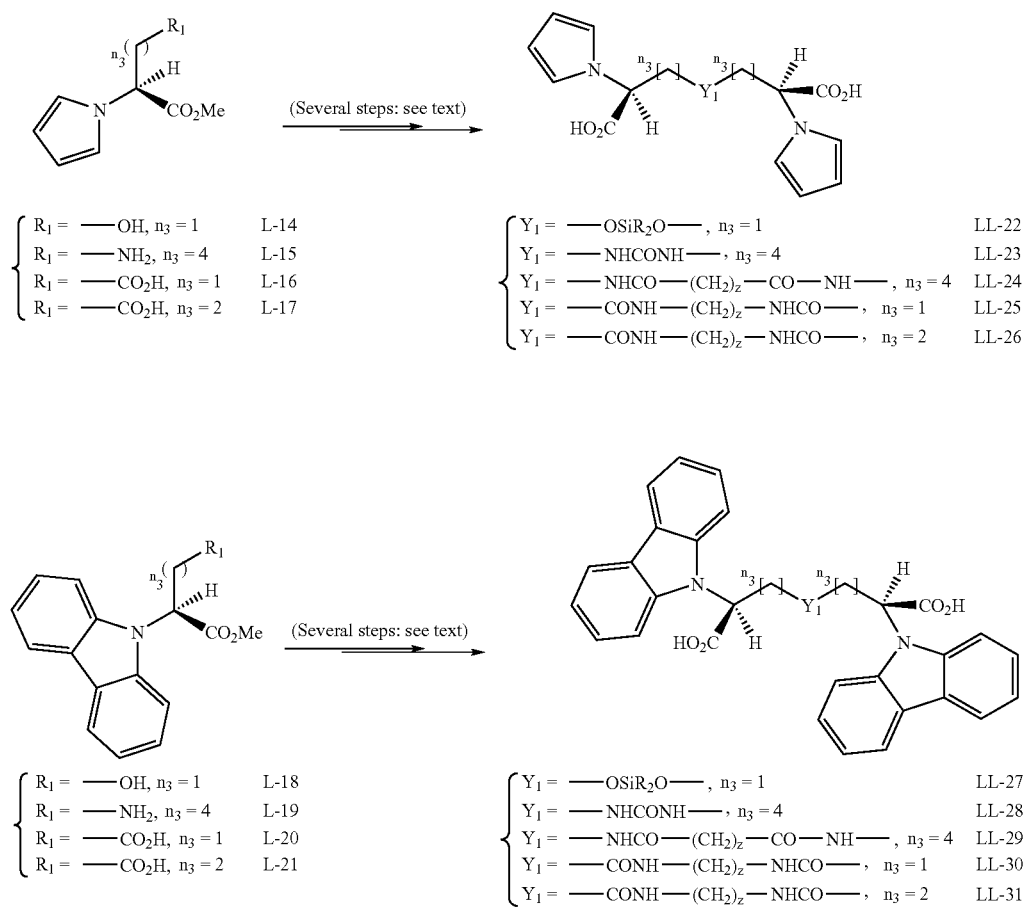

SCHEME 2-continued

C2-Symmetrical dipyrrole, dicarbazole and pseudo-symmetrical pyrrole-carbazole oxidizable monomers

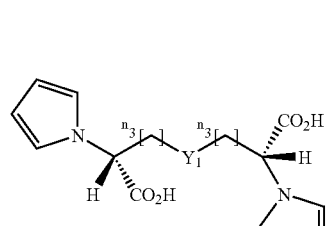

DD-32/DD-36

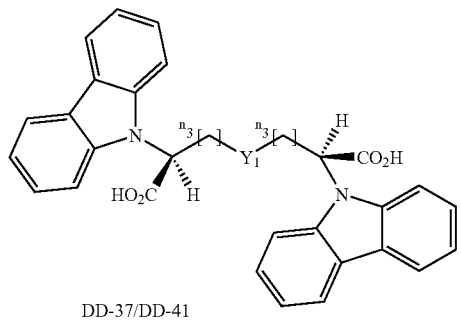

DD-37/DD-41

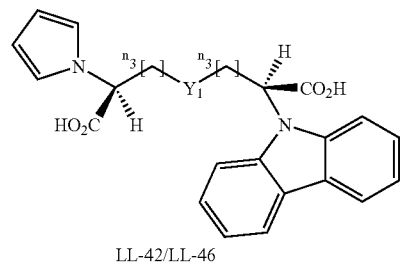

LL-42/LL-46

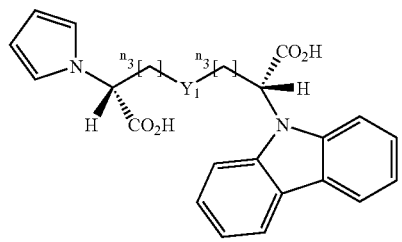

DD-47/DD-51

$Y_1$ and $n_3$: same values as above

SCHEME 2a

C2-Symmetrical dipyrrole and dicarbazole

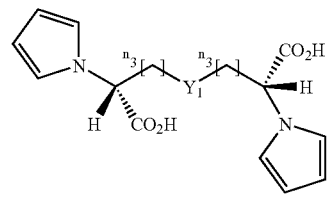

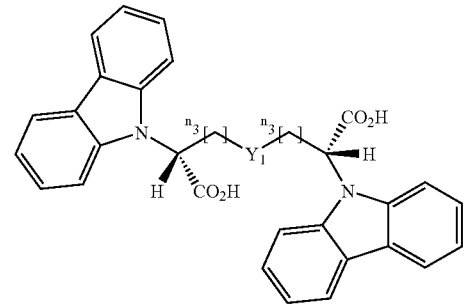

| | | |
|---|---|---|
| $Y_1 =$ —OSiR$_2$O—, $n_3 = 1$ | DD-32 | DD-37 |
| $Y_1 =$ —NHCONH—, $n_3 = 4$ | DD-33 | DD-38 |
| $Y_1 =$ —NHCO—(CH$_2$)$_z$—CO—NH—, $n_3 = 4$ | DD-34 | DD-39 |
| $Y_1 =$ —CONH—(CH$_2$)$_z$—NHCO—, $n_3 = 1$ | DD-35 | DD-40 |
| $Y_1 =$ —CONH—(CH$_2$)$_z$—NHCO—, $n_3 = 2$ | DD-36 | DD-41 |

SCHEME 2b

C2 pseudo-symmetrical pyrrole-carbazole oxidizable monomers

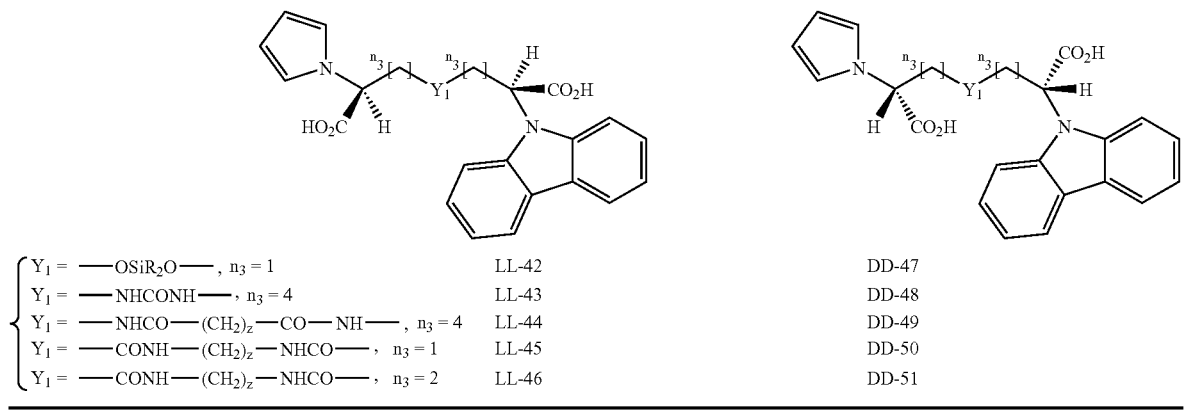

$$\begin{cases} Y_1 = \text{—OSiR}_2\text{O—}, \ n_3 = 1 & \text{LL-42} & \text{DD-47} \\ Y_1 = \text{—NHCONH—}, \ n_3 = 4 & \text{LL-43} & \text{DD-48} \\ Y_1 = \text{—NHCO—(CH}_2)_z\text{—CO—NH—}, \ n_3 = 4 & \text{LL-44} & \text{DD-49} \\ Y_1 = \text{—CONH—(CH}_2)_z\text{—NHCO—}, \ n_3 = 1 & \text{LL-45} & \text{DD-50} \\ Y_1 = \text{—CONH—(CH}_2)_z\text{—NHCO—}, \ n_3 = 2 & \text{LL-46} & \text{DD-51} \end{cases}$$

SCHEME 3

Nanoparticles and magnetically responsive nanoparticles for covalent grafting of biological ligands

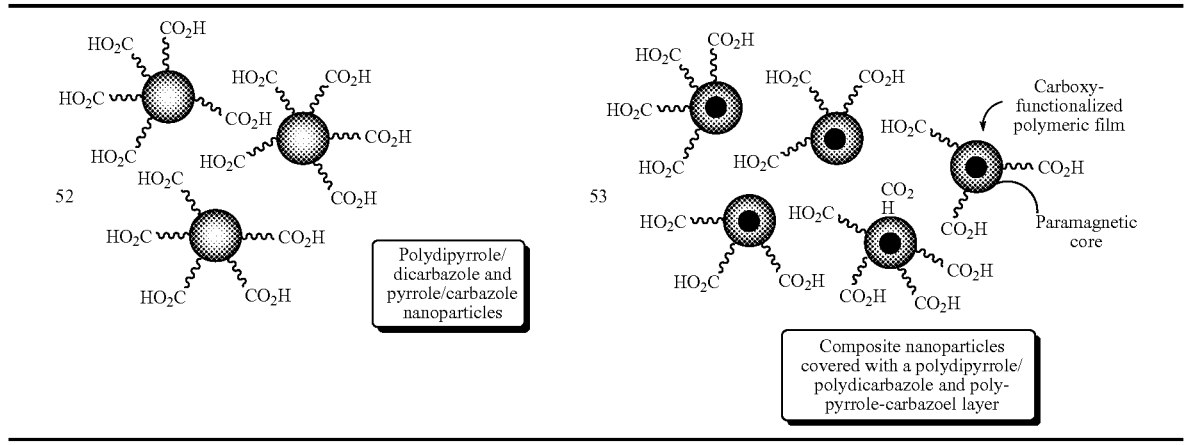

Further manipulation of surface functionality of nanoparticles 52-53 (Scheme 3) takes advantage of the fact that carboxylates can be modified to virtually any kind of surface groups using amide coupling chemistry involving water-soluble carbodiimides. Copolymerization with added biotinylated or protein-repellant PEG-pyrrole (or carbazole) monomers 54-55, wherein $n_4$ represents an integer from 1 to 200, in various ratios affords dually functionalized copolymer nanoparticles and magnetic nanocomposite particles combining two orthogonal functional groups (—COX and —CH$_2$-biotin or —CH$_2$OMe) in one type of polymeric or composite support.

The above mentioned monomers have been electrochemically characterized, emphasizing the production of electro-conductive carboxylated films for covalent grafting of amino-containing biological probes (DNA/cDNA/RNA and proteins or antibodies) onto conductive indium tin oxide electrode (ITO), as an example of transparent conductive surface electrode. Applications of the related diagnostic biochips by surface micro- and nano-arraying are clear to one skilled in the atr.

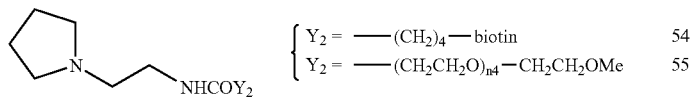

$$\begin{cases} Y_2 = \text{—(CH}_2)_4\text{—biotin} & 54 \\ Y_2 = \text{—(CH}_2\text{CH}_2\text{O)}_{n4}\text{—CH}_2\text{CH}_2\text{OMe} & 55 \end{cases}$$

B. Epitaxial Growth of Conductive Polymers (ECPs) onto SAM-Modified ITO Electrodes Compact, thin (<30 Angstrom) and chemically stable pyrrole-, dipyrrole-, carbazole-, dicarbazole- or hybrid pyrrole-carbazole siloxane-containing self-assembled monolayers (SAMs) have been used to engineer ITO hydroxylated surfaces for covalent attachment of biological ligands. Such films are prepared from precursors 63-69 (scheme 5) and are covalently anchored onto ITO electrodes (Scheme 4) using known SAM technologies. The hydrocarbon chains of these layers are perpendicular to the surface and present an external array of pendant pyrrole or carbazole groups which are electrochemically oxidizable to the corresponding surface-confined radical cations. Such planar, oxidizable arrays provide structured adhesive adlayers (i.e., very thin generally mono-atomic or nanometric interlayers of a second compound that connects the electrode to the medium) for the further oxidative formation of epitaxially grown poly(heteroarene) films whose precursors are dissolved in the surrounding solutions. Surface-confined radical cations are suggested to covalently attach to the poly(heteroarene) films, thereby anchoring the polymers to the surfaces.

Providing that the polymer precursors bear an appropriate amount of functional groups (Fs) for post-polymerization coupling chemistry with biological ligands (e.g., proteins, antibodies, DNA/cDNA/RNA sequences, and the like), such an approach allows design of polar hydroxylated ITO surfaces for biological applications (Scheme 4).

The synthesis, characterization and application of N-(3-(trimethoxysilyl)propyl)pyrole 56 as a derivatizing reagent for n-type silicon electrodes, is known. The pendant pyrrol functionalities, were used to covalently anchor non functional polypyrrole grown, anodically from a 1.0 M pyrrole solution in $CH_3CN$. As shown by tape peel tests, the adhesion of the thick, conducting polypyrrole films is dramatically enhanced compared to underivatized electrodes. Similar results have been obtained using the thiolated pyrroles 57-62 spontaneously adsorbed on gold electrodes. Such SAMs were demonstrated to be strongly adhesive substrates for the electrooxidative formation of robust, dense and smooth polypyrrole films.

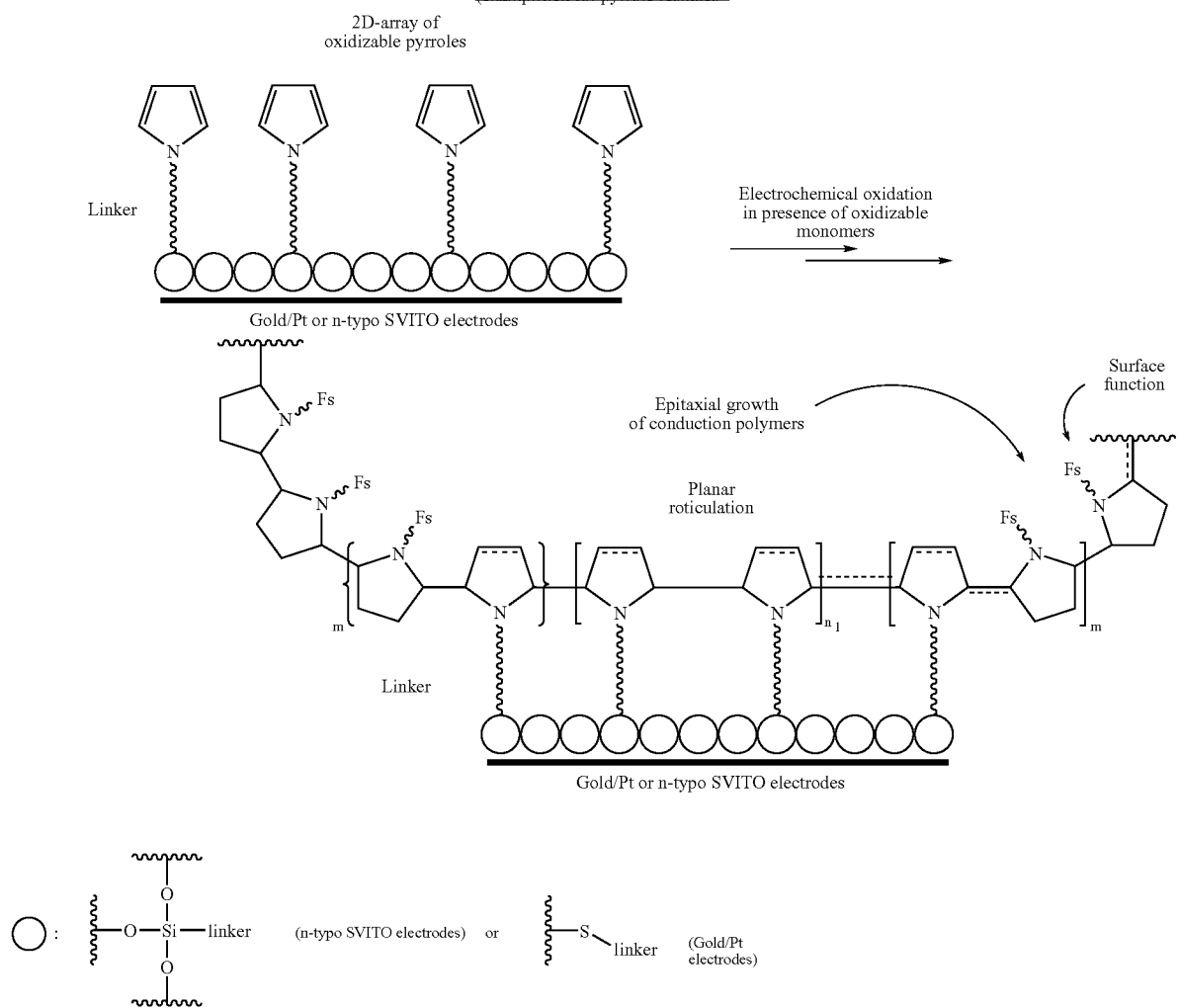

Scheme 4:
Epitaxial growth of functional ECPs onto SAM-modified ITO electrodes (examplified for pyrrole residues)

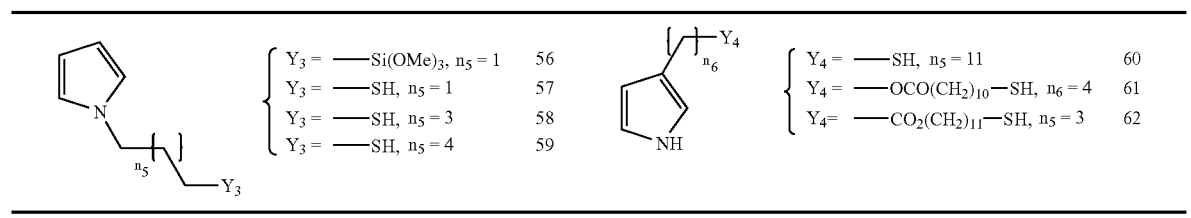

When fabricated as simple thiolated self-assembled monolayers chemisorbed onto gold, composite polypyrrole films resisted reductive desorption. This increase in stability of the polymerized polypyrrole films is attributable to the multiple thiol-gold bonds linking the thiolated composite polymers to the gold surface.

Scheme 5 shows the siloxane form of the monomers, oxidizable pyyrole- (63), carbazole- (64), dipyrrole- (65 and 67), dicarbazole- (66 and 68), and the hybrid pyrrole-carbazole- (69) designed for the corresponding siloxane-anchored self-assembled monolayers. Interestingly, compounds 63-69 may contain one or two —Si(OMe)$_3$ groups, providing one or two anchoring Si-functions. The silane moiety is useful for anchoring the pyrrole/carbazole unit of 63-69 onto the ITO electrode to be further operated oxidatively in the presence of the monomers of the present invention and epitaxially anchor the corresponding chiral polymers which are useful, for example, for grafting ligands.

They are synthesized readily by alkylation of the related ω-brominated alkyltrimethoxysilanes by pyrrolyl- and carbazolyllithium or by amide coupling of related carboxylates with ω-amino alkyltrimethoxysilanes. After preparation of the monolayers on the conducting glass substrates (by controlled hydrolysis), such monolayers possessing pendant pyrrole or carbazole groups are exposed to solutions of monomers of present invention, for example LL-22/LL-51 (Scheme 3) and electrooxidized anodically to the corresponding poly(pyrrole), poly(carbazole) and poly(pyrrole-carbazole) films, anchored on the siloxane-SAMs Much experimental effort was invested in: (1) testing and characterizing the formation of oxidizable siloxane monolayers on ITO surfaces (from compounds 63-69), (2) optimization of the preferred monomer of the types 63-69 (for SAMs formation) and monomers of the present invention, for example LL-22/LL-51 (for epitaxial growth of the corresponding polymers), (3) optimizing the oxidative electrochemical conditions for the production of the carboxylated polymers anchored to the self-assembled monolayers, and (4) testing the post-polymerization carboxylate activation of the chiral composite consisting the carboxylated-films to what extent is indeed accessible for further covalent attachment of biological ligands.

Scheme 5
Oxidization silanes 63-69 for SAM preparation on ITO electrodes ($n_7$ = 0-30)

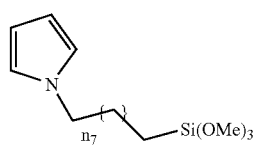

63

-continued

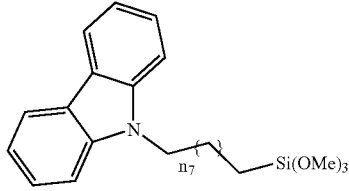

64

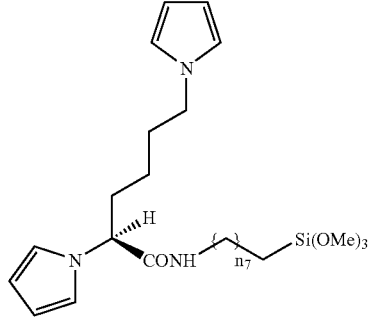

65

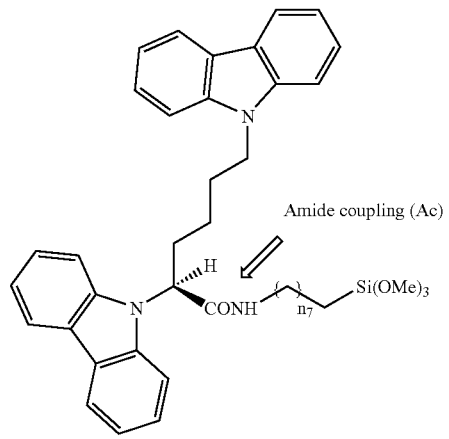

66

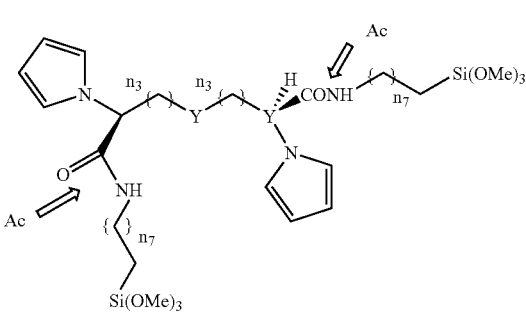

67

-continued

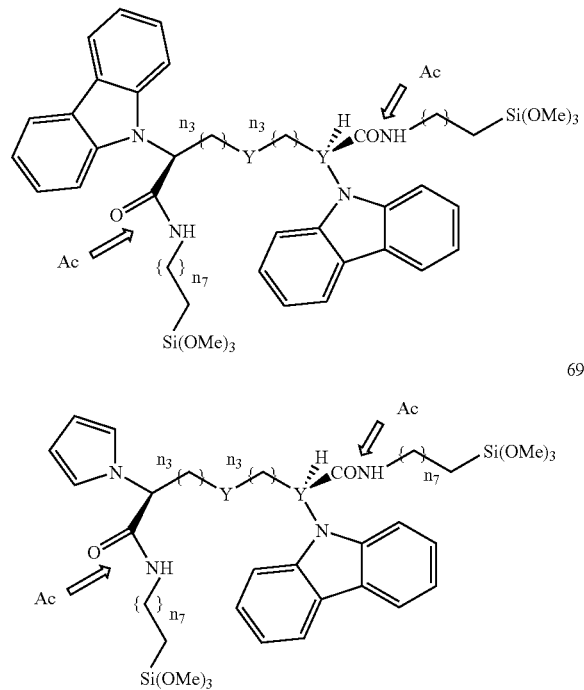

C. Arrays of Gold Nanodots and Electroconductive Polymers (ECPs). Arrays of Composite Au-Polymers Nanoelectrodes and Nanoscaled Functionalized Polymeric Cylinders It was experimentally demonstrated that monodisperse gold nanoparticles dispersed in a polypyrrole matrix, resulted in novel polymer-metal composite nanomaterials. In this context and according to Scheme 6, it becomes possible to functionalize ITO electrodes with nanostructured arrays of conductive gold dots, and to create electrically insulating siloxane monolayers (SAMs) to profoundly modify the characteristics of those surfaces. Due to the high affinity of hydrolyzable siloxanes of the type $Me\text{-}(CH_2)_{n_8}\text{-}Si(OR')_3$ for hydroxylated surfaces like ITO (while they are not chemisorbed on gold), it is possible to prepare ITO surfaces of type 70 (Scheme 6) containing two structured but segregated domains, one insulating corresponding to the siloxane-SAMs (for $n_8 > 10$, $h_1 \geq 15$ nm, surface of type 70) and the second conductive and left unmodified (the array of gold nanodots) possessing a lateral periodicity reminiscent of the original gold nanodots pattern. Such conductive gold nanodots arrays, while embedded in the SAM layer, can be functionalized by anodically polymerizing dipyrrole, dicarbazole or pyrrole-carbazole monomers having the functional group —COX to obtain engineered surfaces modified by composite gold-polymer nanostructures (and nanowells, if desired) of type 71 (Step 1 of the process depicted in Scheme 6). Moreover, since siloxane-SAMs are particularly sensitive to fluoride anions ($nBu_4NF$, anhydrous or aqueous conditions), it is possible to selectively destroy the SAMs pattern leaving an array of nanostructured polymeric electrodes on the ITO surfaces such as 72. The control of the relative dimensions of the siloxane layer ($h_1$) versus gold nanodots height ($h_2$) and of the electrochemical conditions for polymers growth ($h_3$ in arrays of type 72) affords the ITO electrodes 72 nanostructured as arrays of composite gold-polymers nanoelectrodes.

SCHEME 6

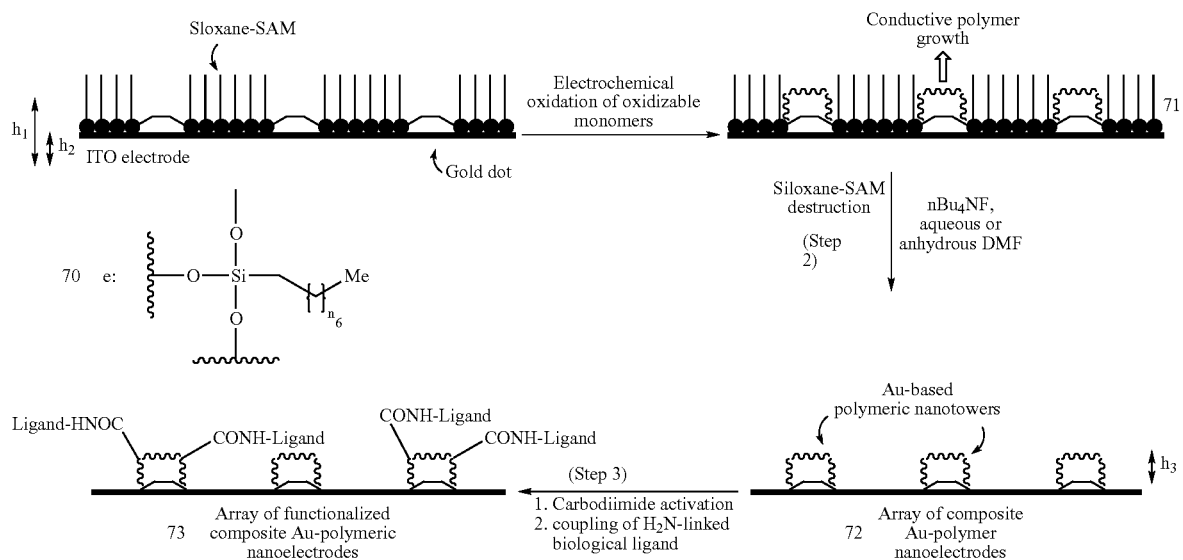

SCHEME 6-continued

Arrays of gold nanodots and ECPs functionalization

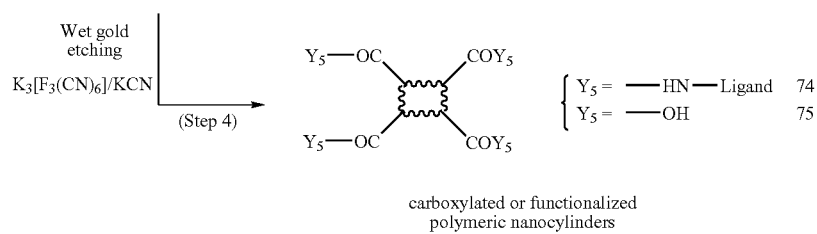

carboxylated or functionalized
polymeric nanocylinders

Due to the presence of carboxylate functions, such surfaces are optionally could be modified with any amine-containing biological ligands as described above (dry or wet carbodiimide activation for amino coupling) to afford surfaces of type 73. Due to the very small diameters of the originally patterned gold nanodots, in the range order of globular proteins, embodiments of surfaces 71-73 are useful as electrochemical transducers, for example, for probing amperometrically enzymatic reactions (GOx or PPO) catalyzed by a limited number of macromolecular proteins when surface-confined by covalent grafting onto the chirally modified nanoelectrodes.

Another interesting feature of this process is exemplified by Step 4 where nanostructured surfaces of type 72 or 73 are subsequently contacted with known gold etching solutions such as 0.002 M $K_3[Fe(CN)]_6$/0.1 M KCN releasing polymeric carboxylated-poly(dipyrrole), poly(dicarbazole) and poly(pyrrole-carbazole) nanocylinders 74-75 of controlled nanometric dimensions. In the cases where very smooth etching protocols are not compatible with already grafted biomolecules (for example, case of 74 from 73, proteins, DNA/cDNA and RNA), post-release grafting procedures involving the polymeric matrix carboxylates are applied from 75 (acid form) to afford chiral nanostructures 74 of the desired biological functionalization. This allows the use of gold spherical nanoparticles as templates for the preparation of hollow polypyrrole and poly(N-methylpyrrole) surfaces. Such surfaces are useful, for example, for drug delivery.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Example 1

Preparation of a Chiral Dipyrrole Polymerizable Monomer

Scheme of Synthesis of Optically Active
(L)-2,6-dipyrrole-1-yl-hexanoic acid

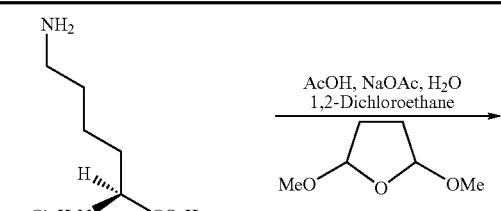

2,6-Diamino-hexanoic acid
monohydrochloride $C_6H_{15}O_2N_2Cl$
Mol Wt: 182.65
C 36.06; H 7.78; O 13.72; N 12.02; Cl 30.41

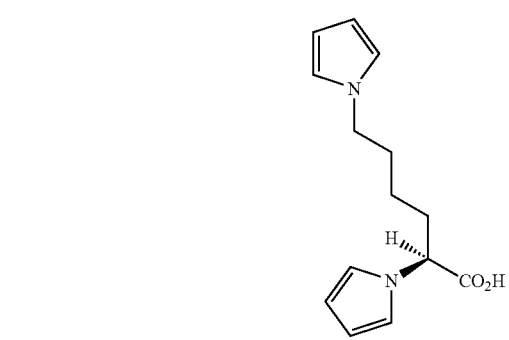

2,6-Dipyrrol-1-yl
hexanoic acid $C_{14}H_{18}N_2O_2$
Mol Wt: 246.14
C 69.20; H 7.74; O 12.29; N 10.76

Reagents:

| | | |
|---|---|---|
| 0.822 g | 4.5 mmol | L-Lysine monohydrochloride |
| 1.31 mL | 10.2 mmol | 2,5-Dimethoxytetrahydrofuran |
| 0.7384 g | 9.0 mmol | Sodium acetate |
| 4.95 mL | | Water |
| 2.475 mL | | Acetic acid |

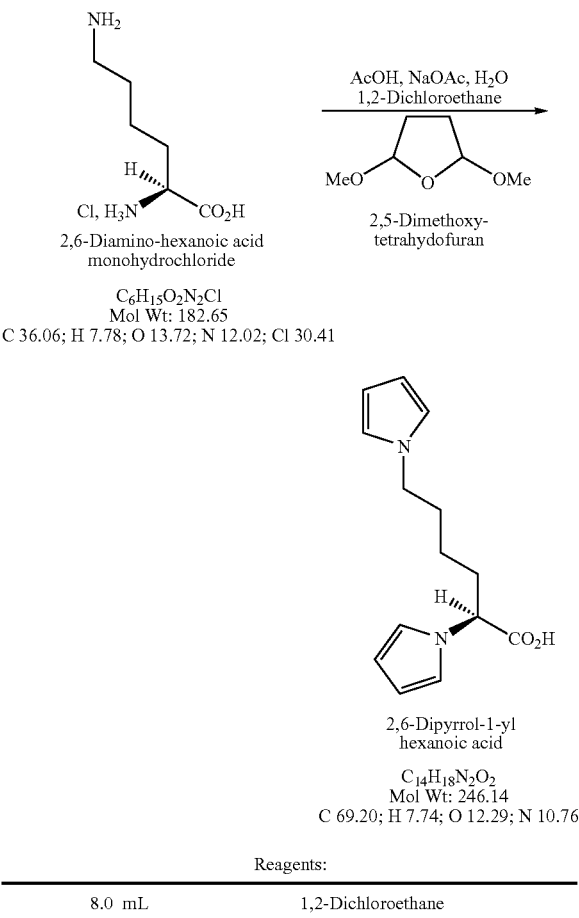

sodium acetate (0.7384 g, 9.0 mmol), acetic acid (2.475 mL), 1,2-dichloroethane (5.0 mL) and water (4.95 mL). The medium is refluxed during 4 hours at 76° C. After cooling, a saturated solution of ammonium chloride is added to the solution mixture (30.0 mL). The aqueous solution is then extracted with diethyl ether (5×30 ml+10 ml wash), dried over anhydrous $MgSO_4$, filtrated (Buchner 5 mm) and evaporated under vacuum. The crude brown dipyrrole-acid is purified by two successive column chromatography steps on silica gel Si-60 (Merck), 45-63 mm using the following solvent mixtures:

1) first column 5 g $SiO_2$, $CH_2Cl_2$:EtOH 9:1 100 ml, $CH_2Cl_2$:EtOH 8:2 300 ml, $R_{f=0.41}$ (analytical TLC onto Si—$F_{254}$ Merck, UV-revelation).
2) second column, 10 g $SiO_2$, $CH_2Cl_2$:EtOH 9:1 150 ml, $CH_2Cl_2$:EtOH 8:2 330 ml.

The purified compound is obtained as a brown mobile oil which is stored protected from light (yield 53.3%).

Structural Analyses $^1H$: NMR ($CDCl_3$, 300 MHz): d (ppm): 6.71 (t, 2.1 Hz, 2H), 6.6 (t, 2.1 Hz, 2H), 6.2 (t, 2.1 Hz, 2H), 6.12 (t, 2.1 Hz, 2H), 4.55 (dd, 9.6 Hz, 5.7 Hz, 1H), 3.82 (td, 6.9 Hz, 2.7 Hz, 1H), 2.19-1.27 (m, 6H);

$^{13}C$:NMR ($CDCl_3$, 75 MHz): d (ppm): 175.25 (CO), 120.68 (CH), 120.33 (CH), 109.03 (CH), 108.29 (CH), 61.92 (CH), 49.39 ($CH_2$), 32.42 ($CH_2$), 31.21 ($CH_2$), 23.45 ($CH_2$);

High-resolution MS (CI, i-Butane): m/z 247.1440 (65.35%, $MH^+$), 246.1384 (100%; calculated mass: 246.1368: differnce in ppm: −6.5);

FT-IR (KBr) (n, $cm^{-1}$): 3587 ($n_{O-H}$); 2513 ($n_{C-H}$); 1809 ($n_{C=O}$); 1672, 1625 ($n_{c=c}$); 1491, 1439, 1382 ($n_{C-H}$); 1199 ($n_{C-O}$); 1041 ($n_{=C-H}$);

Analytical HPLC for Optical Activity of the Dipyrrole-Acid:

Diastereoisomeric amides of (S)-alpha-(−)-methylbenzyl amine obtained by a usual DMAP-catalyzed coupling (DCC, catalytic DMAP, $CH_2Cl_2$, 2 hrs, 20° C.) performed with the dipyrrole-acid prepared according to the above synthesis [Column LichroCART 125-4 mm, LichroSpher Si 60 (4 mm×125 mm) eluted by the mixture petroleum ether: AcOEt 90/10. UV detection is operated at 247.5 nm. The retention times of the two diastereoisomeric amides are: $t_R$=4.40 min and 6.00 min for a solvent flow of 2.0 mL/min. Integration of the two UV peaks furnish an enantiomeric enrichment (ee) of 90.0% indicating a minimal erosion of the enantiomeric purity of the starting dipyrrole-acid.

A Typical Experimental Protocol (Entry 5 of the Hereunder Table of Complementary Results):

2,5-Dimethoxytetrahydrofuran (DMT, 1.31 mL, 10.2 mmol) dissolved in 1,2-dichloroethane (3.0 mL) is added dropwise, during 2 hours, under a nitrogen atmosphere, to a round bottom flask (50 mL) containing the following biphasic mixture of L-lysine monohydrochloride (0.822 g, 4.5 mmol),

| | L-lysine.HCl (mmole) | DMT (mmole) | Solvent | Temp. [° C.] | Time (hrs) | Yield |
|---|---|---|---|---|---|---|
| 1 | 4.5 | 10.2 | $CH_3CO_2H/CH_3CO_2Na/H_2O/ClCH_2CH_2Cl$ | 76 | 4 | 65.0% |
| 2 | 4.5 | 10.2 | $CH_3CO_2H/CH_3CO_2Na/H_2O/ClCH_2CH_2Cl$ | 76 | 4 | 55.6% |
| 3 | 4.5 | 10.2 | $CH_3CO_2H/CH_3CO_2Na/H_2O/ClCH_2CH_2Cl$ | 76 | 4 | 57.6% |
| 4 | 9.0 | 20.4 | $CH_3CO_2H/CH_3CO_2Na/H_2O/ClCH_2CH_2Cl$ | 76 | 4 | 40.2% |
| 5 | 4.5 | 10.2 | $CH_3CO_2H/CH_3CO_2Na/H_2O/ClCH_2CH_2Cl$ | 76 | 4 | 53.3% |
| 6 | 4.5 | 10.2 | $CH_3CO_2H$/pyridine/$H_2O$/$ClCH_2CH_2Cl$ | 76 | 4 | 36.4% |
| 7 | 4.5 | 10.2 | $CH_3CO_2H$/pyridine/$H_2O$/$ClCH_2CH_2Cl$ | 76 | 4.5 | 50.7% |
| 8 | 4.5 | 10.2 | $CH_3CO_2H$/pyridine/$H_2O$/$ClCH_2CH_2Cl$ | 76 | 4 | 29.5% |

Table of complementary results for yield optimization

Example 2

Preparation of a C2-Symetrical Chiral Dipyrrole Polymerizable Monomer Synthesis of (LL)-Cysteine Dipyrrole Dimethyl Ester Scheme of Synthesis of Optically Active (LL)-Cystine Dipyrrole Dimethyl Ester

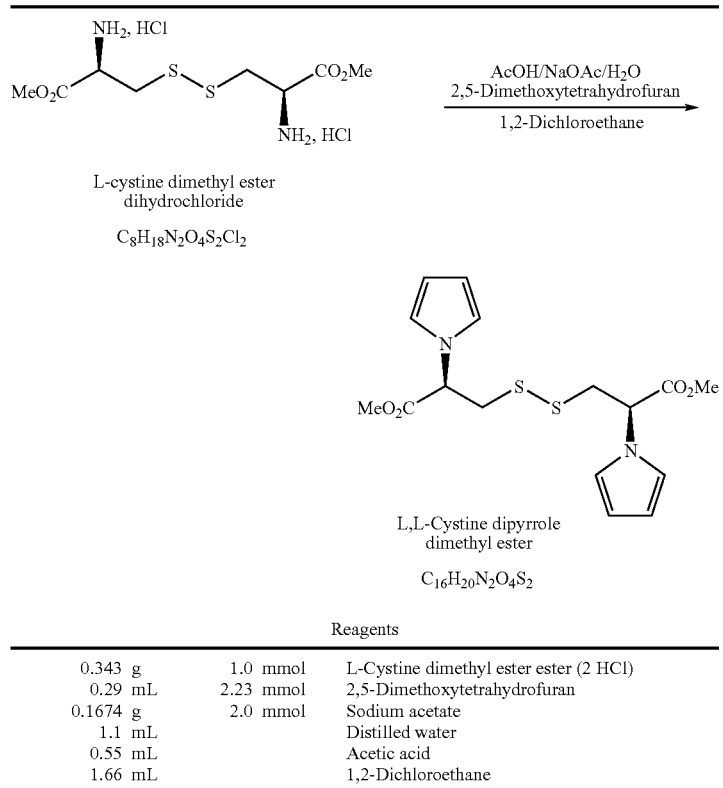

| | | Reagents |
|---|---|---|
| 0.343 g | 1.0 mmol | L-Cystine dimethyl ester ester (2 HCl) |
| 0.29 mL | 2.23 mmol | 2,5-Dimethoxytetrahydrofuran |
| 0.1674 g | 2.0 mmol | Sodium acetate |
| 1.1 mL | | Distilled water |
| 0.55 mL | | Acetic acid |
| 1.66 mL | | 1,2-Dichloroethane |

A Typical Experimental Protocol:

2,5-Dimethoxytetrahydrofuran (DMT, 0.29 mL, 2.23 mmol) was added to around bottom flask (50 mL) containing the following biphasic mixture of L-Cystine dimethyl ester dihydrochloride 98% purity (Aldrich, 0.343 g, 1.0 mmol), sodium acetate (0.1674 g, 2.0 mmol), acetic acid (0.55 mL), 1,2-dichloroethane (1.66 mL) and distilled water (1.1 mL). The medium is refluxed during 4 hours at 76° C. under a nitrogen atmosphere. After cooling to room temperature, dichlormethane (198 mL) is added to the reaction mixture. The separated organic layer is then extracted with water (5×290 mL), dried over anhydrous $MgSO_4$, filtrated (5 micrometer Buchner filter) and evaporated under vacuum. The crude orange oil is purified by two successive column chromatographies on silica gel Si-60 (Merck) 43-60 mm, using the following solvent mixtures:

1) first column, 25 g: $SiO_2$, diethyl ether 400 ml, $R_f$=0.67 (analytical TLC onto Si—$F_{254}$ Merck, UV-revelation).
2) second column, 25 g $SiO_2$, $CH_2Cl_2$/EtOH 9/1 450 ml.

The purified dipyrrole ester is obtained as a yellow oil which is stored at 4° C. away from light (yield 25%).

Structural Analyses $^1$H: NMR ($CDCl_3$, 300 MHz): d (ppm): 6.80 (t, 2.1 Hz, 2H), 6.30 (t, 2.1 Hz, 2H), 5.10-4.90 (m, 1H), 3.78-3.63 (dd, 3H), 3.40 (m, 1H), 3.20 (dd, 3.9 Hz, 1.2 Hz, 1H);

$^{13}$C:NMR ($CDCl_3$, 75 MHz): d (ppm): 169.80 (CO), 169.70 (CO), 120.33 (CH), 109.74 (CH), 109.66 (CH), 109.60 (CH), 109.35 (CH), 60.95 (CH), 60.58 (CH), 53.27 (CH), 53.20 (CH), 33.96 ($CH_2$), 33.33 ($CH_2$);

High-resolution MS (CI, i-Butane): m/z 369.093109 (16.94%, MH$^+$), (calculated mass: 369.094276: 3.2 ppm difference).

Example 3

COOH-Polypyrrole/Polycarbazole Paramagnetic Nanocomposite Particles: Standard Robust Experimental Protocols I. Magnetite Nanoparticle The magnetite paramagnetic nanoparticles were prepared acccording to modifications of the standard aqueous precipitation technique of $Fe^{2+}$ and $Fe^{3+}$ ions from a basic solution (I. R. Massart, *IEEE Trans. Magn.* 1981, 17: p. 131). Aqueous solutions of $FeCl_3$ (160.0 mg, 3.0 ml $H_2O$) and $FeCl_2$ (65.0 mg, 3.0 ml $H_2O$, concentrations ratio 2:1) were mixed at 20° C. and the reaction mixture placed in an ultrasonic water bath. Aqueous ammonium hydroxide (32% 0.3 ml) was added slowly in one portion. A black suspension of magnetite was immediately formed. Following an equilibration period of about 1 minute at room temperature (pH 9), the magnetite nanoparticles were washed several times with distilled water using magnetic decantation till neutrality, and stored in distilled water (magnetite concentration: 16.1 mg/ml suspension, average particle diameter: 10-16 nm by TEM, magnetite nature fully characterized by FT-IR). Typically, the freshly prepared magnetite nanoparticles were immediately engaged in the preparation of COOH-polypyrrole/polycarbazole paramagnetic nanocomposites.

II. Nanocomposite Particles Coated by COOH-Polypyrrole/Polycarbazole Polymers

II a. COOH-Polypyrrole Coverage

The polymerization of a chiral dipyrrole monocarboxylate (as a standard oxidizable monomer) derived from L-lysine was performed in an ultrasonic water bath at room temperature (bath temperature). The pyrrole monomer solution (100.0 mg in 2 ml of methanol) was slowly added to a suspension of freshly prepared magnetite nanoparticles (3.5 ml of distilled ultrapure water). A solution of the $FeCl_3.6H_2O$ oxidizer (500 mg, 2.0 ml of water) was added and the reaction mixture sonicated at 55° C. for 5 h (pH ~2, reactor internal temperature). The nanocomposite particles were washed several times with water, with a MES buffer (pH 5), with a neutral PB buffer, a neutral PBS buffer, and a TNET buffer, then incubated with shaking for 5 min at 65° C. in the same TNET buffer, again with water, acetone, water again, and, stored in a neutral PBS buffer. The final nanocomposite concentration was 3% weight/suspension volume. The whole set of analytical and spectroscopical analyses has been performed on this material (elemental analyses, TGA and FT-IR data, magnetism and coercivity measurements).

IIa. COOH-Polycarbazole Coverage

The exact polymerization precedure for a chiral dicarbazole monocarboxylate (as a standard oxidizable carbazole monomer) derived from L-lysine was similarly performed in a ultrasonic water bath at room temperature (bath temperature) as above. Freshly prepared magnetite nanoparticles (from a mixture of $FeCl_3$ (50.0 mg, 2.0 ml $H_2O$) and $FeCl_2$ (18.0 mg, 2.0 ml $H_2O$)), and 0.35 ml of a 32% aqueous solution of ammonium hydroxide. Resulting magnetite nanoparticles were redispersed in 3.5 ml of methanol. The dicarbazole COOH-monomer (50.0 mg) was dissolved in 3.0 ml of acetone and added to the previous methanol suspension of magnetite nanoparticles. The reaction suspension was sonicated for min and the cerium-based-CAN oxidizer solution (CAN, 70.0 mg, 3.0 ml acetone) was slowly added. The reaction mixture was sonicated at 55° C. (reactor internal temperature) for 5 h (solution pH~2). The nanocomposite particles were washed several times with water, with a MES (pH 5) buffer, with a neutral PB buffer, with a neutral PBS buffer, with a TNET buffer, and incubated with shaking for 5 min at 65° C. in the same TNET buffer, washed again with neutral water, with acetone, and finally with water. The final COOH-polycarbazole paramagnetic nanocomposites are stored in a neutral PBS buffer at a final concentration of 3% weight/volume (suspension, average nanocomposite diameter: 15-20 nm by TEM). The two standard experimental polymerizations described above have been checked for several dicarbazole monomers with similar results and analytical/spectroscopic analyses.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that, fall within the spirit and broad scope of the appended claims. All publications, patents and patent applications mentioned in this specification are herein incorporated in their entirety by reference into the specification, to the same extent as if each individual publication, patent and patent application was specifically and individually indicated to be incorporated herein by reference. In addition, citation or identification of any reference in this application shall not be construed as an admission that such reference is available as prior art to the present invention.

The present invention is not to be limited in scope by the specific embodiments described herein. Indeed, various modifications of the invention in addition to those described herein will become apparent to those skilled in the art from the foregoing description and the accompanying schemes. Such modifications are intended to fall within the scope of the appended claims.

Patents, patent applications, publications, procedures, and the like are cited throughout this application, the disclosures of which are incorporated herein by reference in their entireties. To the extent that a conflict may exist between the specification and a reference, the language of the disclosure made herein controls.

What is claimed is:

1. An optical active polymerizable monomer containing at least two oxidizable groups and at least two chiral centers of the general formula:

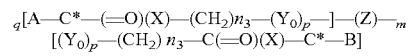

wherein,

—C(=O)(X) represents an activated carboxyl group capable of binding a functional group or a ligand; wherein such binding may occur pre- or post- (co)polymerization process, and when —C(=O)(X) represents a free carboxylic group also a salt of such a free carboxylic group;

X represents a moiety of a molecule capable of reacting with a nucleophile group;

A and B are the same or different oxidizable group;

Z represents a two- to six-valence center, resulting in a C2-C6 symmetric or pseudo-symmetric monomer;

$Y_0$ represents a divalent radical which links the center of said C2-C6 symmetric or pseudo-symmetric monomer to the $(CH_2)$—$n_3$ chain;

p is an integer selected from 0 or 1;

$n_3$ is an integer from 0-100;

q and m each represents an integer from 1-5; provided that the sum of q +m is an integer from 2 to 6; and wherein the sign * signifies that an associated carbon atom is an active optical center.

2. The polymerizable monomer according to claim 1, wherein each of the chiral carbon links a carboxylated functional group that is capable of binding a ligand.

3. The polymerizable monomer according to claim 1, wherein at least one of the oxidizable groups A and B is selected from the group consisting of pyrrole and carbazole.

4. The polymerizable monomer according to claim 1, wherein A and B oxidizable groups are the same and said monomer may appear in the form of C2-C6 symmetrical structures.

5. The polymerizable monomer according to claim 4, wherein said oxidizable group is selected from the group consisting of pyrrole or carbazole.

6. The polymerizable monomer according to claim 4, wherein said monomer is dipyrrole.

7. The polymerizable monomer according to claim 4, wherein said monomer is dicarbazole.

8. The polymerizable monomer according to claim 1, wherein A and B oxidizable groups are not same and said monomer may appear in the form of C2-C6 pseudo-symmetrical structures.

9. The polymerizable monomer according to claim 8, wherein said oxidizable groups are pyrrole and carbazole.

10. The polymerizable monomer according to claim 1, wherein said monomer is electropolymerizable.

11. The polymerizable monomer according to claim 1, wherein X represents —$OR_3$ or —$SR_3$ group, in which $R_3$ represents hydrogen, an organic group, metal or any other positive ion.

12. The polymerizable monomer according to claim 11, wherein $R_3$ represents optionally substituted aliphatic, cyclic, aromatic or heterocyclic group and any combination thereof.

13. The polymerizable monomer according to claim 12, wherein $R_3$ represents —N-succinimide, —N-phthalimide, pentafluorophenyl, a biotin group, a sugar group or 1,2-/1,3-amino alcohol group.

14. The polymerizable monomer according to claim 11, wherein $R_3$ represents optionally substituted alkyl, cycloalkyl and aryl.

15. A polymerizable monomer according to claim 1, wherein X represents $NR_1R_2$ wherein $R_1$ and $R_2$ each represents H or an organic group.

16. The polymerizable monomer according to claim 1, wherein each carboxylated functional group is capable of binding a ligand, at either pre- and/or post-(co)polymerization step.

17. The polymerizable monomer according to claim 1, wherein the oxidizable groups A and B may be the same or different, and each independently is selected from the group consisting of pyyrole, dicarbazole, acetylene, azine, p-phenylene, p-phenylene-vinylene, pyrene, thiophene, furan, selenophene, pyridazine, aniline and tyramine.

18. The polymerizable monomer according to claim 1, wherein Z represents a single atom.

19. The polymerizable monomer according to claim 18, wherein Z represents an atom selected from the group consisting of C, N, S, Se, Si, O and P.

20. The polymerizable monomer according to claim 1, wherein Z represents a group of atoms.

21. The polymerizable monomer according to claim 20, wherein Z represents a group of atoms selected from the group consisting of —O—$Si(R_1)(R_2)$—O—; —O—Si(—O—)(—O—)—O—; —O—Si(—O—)($R_1$)—O—; CO; $CH_2$; CH; HNCO; HNCONH; NCON; —S—S—; linear or branched hydrocarbon chain; cyclo-hydrocarbon; aromatic and hetercyclic rings;
wherein $R_1$ and $R_2$ are the same or different, each representing a monovalent radical.

22. The polymerizable monomer according to claim 1, wherein $Y_0$ represents an optionally substituted linear or branched alkylene ($C_1$-$C_{30}$) and optionally substituted arylene or alkarylene or aralkylene.

23. A polymerizable monomer according to claim 1, wherein $Y_1$ represents the group HNCONH; —NHCO—$(CH_2)_t$—CONH—, —CONH—$(CH_2)_t$—NHCO—; wherein t represents an integer from 1 to 20.

24. A polymerizable C2 symmetrical and pseudo-symetrical monomer according to claim 1, selected from the group consisting of (a) to (f):

(a) selected from the group consisting of LL-22, LL-23, LL-24, LL-25 and LL-26:

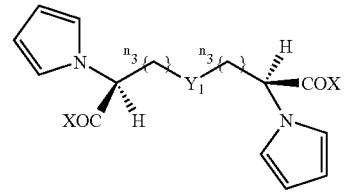

$$\begin{cases} Y_1 = \text{—OSiR}_2\text{O—}, n_3 = 1 & \text{LL-22} \\ Y_1 = \text{—NHCONH—}, n_3 = 4 & \text{LL-23} \\ Y_1 = \text{—NHCO—}(CH_2)_z\text{—CO—NH—}, n_3 = 4 & \text{LL-24} \\ Y_1 = \text{—CONH—}(CH_2)_z\text{—NHCO—}, n_3 = 1 & \text{LL-25} \\ Y_1 = \text{—CONH—}(CH_2)_z\text{—NHCO—}, n_3 = 2 & \text{LL-26} \end{cases}$$

wherein X is as defined in claim 1;

(b) selected from the group consisting of LL-27, LL-28, LL-29, LL-30 and LL-31:

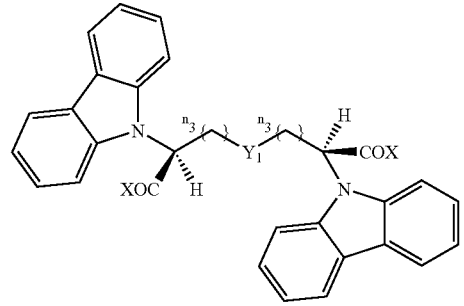

$$\begin{cases} Y_1 = \text{—OSiR}_2\text{O—}, n_3 = 1 & \text{LL-27} \\ Y_1 = \text{—NHCONH—}, n_3 = 4 & \text{LL-28} \\ Y_1 = \text{—NHCO—}(CH_2)_z\text{—CO—NH—}, n_3 = 4 & \text{LL-29} \\ Y_1 = \text{—CONH—}(CH_2)_z\text{—NHCO—}, n_3 = 1 & \text{LL-30} \\ Y_1 = \text{—CONH—}(CH_2)_z\text{—NHCO—}, n_3 = 2 & \text{LL-31} \end{cases}$$

wherein X is as defined in claim 1;

(c) selected from the group consisting of DD-32, DD-33, DD-34, DD-35 and DD-36:

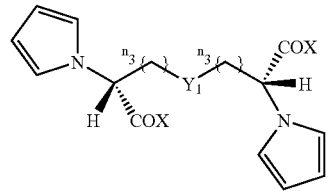

$$\begin{cases} Y_1 = \text{—OSiR}_2\text{O—}, n_3 = 1 & \text{DD-32} \\ Y_1 = \text{—NHCONH—}, n_3 = 4 & \text{DD-33} \\ Y_1 = \text{—NHCO—}(CH_2)_z\text{—CO—NH—}, n_3 = 4 & \text{DD-34} \\ Y_1 = \text{—CONH—}(CH_2)_z\text{—NHCO—}, n_3 = 1 & \text{DD-35} \\ Y_1 = \text{—CONH—}(CH_2)_z\text{—NHCO—}, n_3 = 2 & \text{DD-36} \end{cases}$$

wherein X is as defined in claim 1;

(d) selected from the group consisting of DD-37, DD-38, DD-39, DD-40 and DD-41:

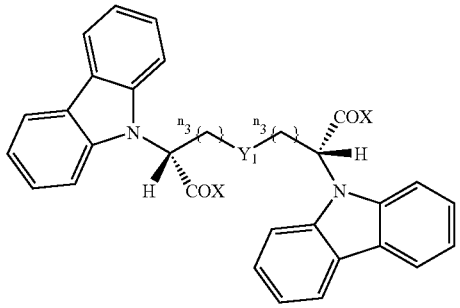

| | |
|---|---|
| $Y_1 = $ —OSiR$_2$O—, $n_3 = 1$ | DD-37 |
| $Y_1 = $ —NHCONH—, $n_3 = 4$ | DD-38 |
| $Y_1 = $ —NHCO—(CH$_2$)$_z$—CO—NH—, $n_3 = 4$ | DD-39 |
| $Y_1 = $ —CONH—(CH$_2$)$_z$—NHCO—, $n_3 = 1$ | DD-40 |
| $Y_1 = $ —CONH—(CH$_2$)$_z$—NHCO—, $n_3 = 2$ | DD-41 | wherein X is as defined in claim 1;

(e) selected from the group consisting of LL-42, LL-43, LL-44, LL-45 and LL-46:

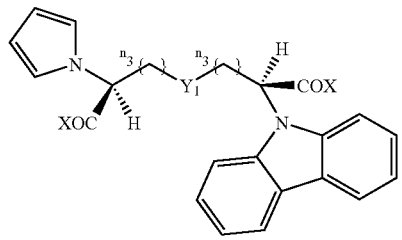

| | |
|---|---|
| $Y_1 = $ —OSiR$_2$O—, $n_3 = 1$ | LL-42 |
| $Y_1 = $ —NHCONH—, $n_3 = 4$ | LL-43 |
| $Y_1 = $ —NHCO—(CH$_2$)$_z$—CO—NH—, $n_3 = 4$ | LL-44 |
| $Y_1 = $ —CONH—(CH$_2$)$_z$—NHCO—, $n_3 = 1$ | LL-45 |
| $Y_1 = $ —CONH—(CH$_2$)$_z$—NHCO—, $n_3 = 2$ | LL-46 | wherein X is as defined in claim 1;

and (f) selected from the group consisting of DD-47, DD-48, DD-49, DD-50 and DD-51:

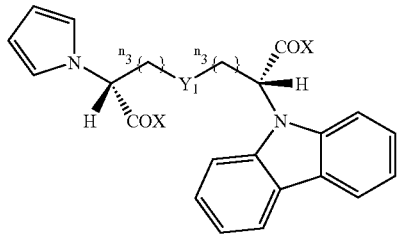

| | |
|---|---|
| $Y_1 = $ —OSiR$_2$O—, $n_3 = 1$ | DD-47 |
| $Y_1 = $ —NHCONH—, $n_3 = 4$ | DD-48 |
| $Y_1 = $ —NHCO—(CH$_2$)$_z$—CO—NH—, $n_3 = 4$ | DD-49 |
| $Y_1 = $ —CONH—(CH$_2$)$_z$—NHCO—, $n_3 = 1$ | DD-50 |
| $Y_1 = $ —CONH—(CH$_2$)$_z$—NHCO—, $n_3 = 2$ | DD-51 | wherein X is as defined in claim 1.

25. A polymerizable C2 symmetrical monomer according to claim 24, wherein $Y_1$ in the compounds defined in groups (a) and (c) represents —S—S— group and $n_3$ represents an integer from 1 to 4.

26. A polymerizable C2 symmetrical and pseudo-symmetrical monomer according to claim 1, selected from the group consisting of monomers 63 to 69:

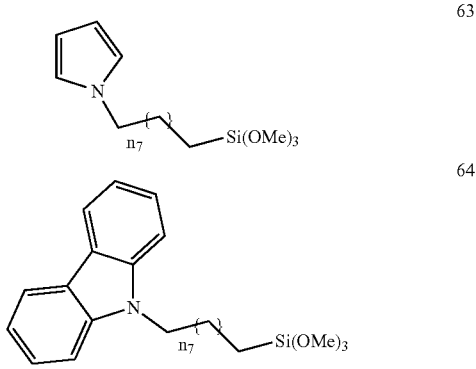

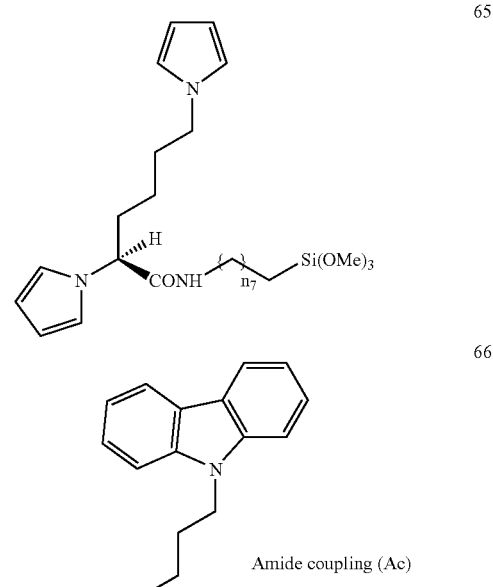

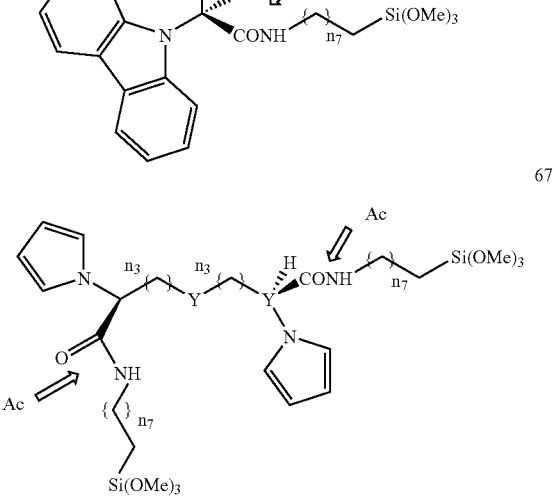

-continued

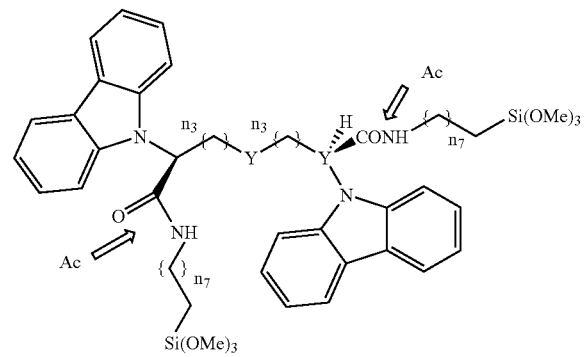

68

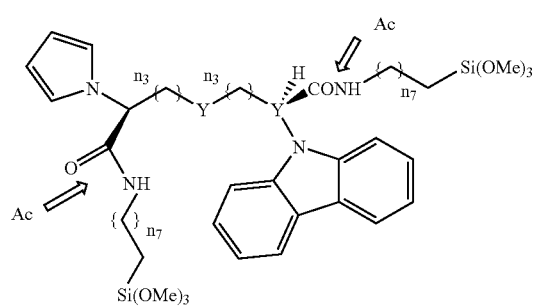

69 wherein $Y_1$ is defined in claim 1, $n_3$ is an integer from 0 to 100 and $n_7$ is an integer from 0 to 30.

27. A polymerizable C3 to C6 symmetrical monomer according to claim 1, selected from the group consisting of:

C3 SYMMETRY

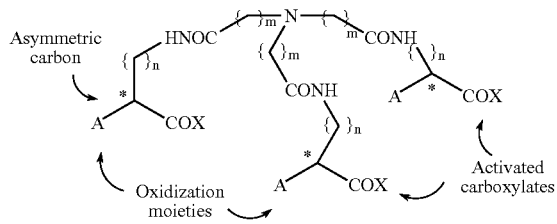

C4 SYMMETRY

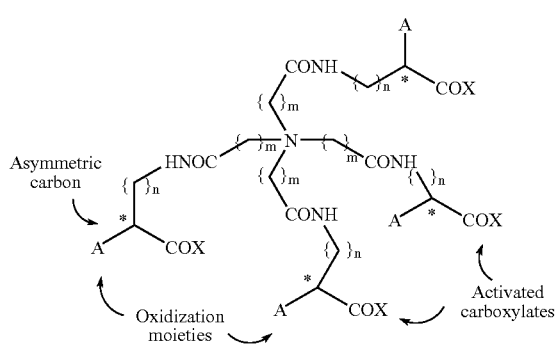

C5 SYMMETRY

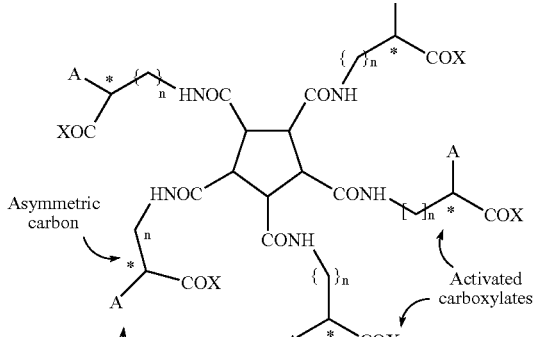

C6 SYMMETRY

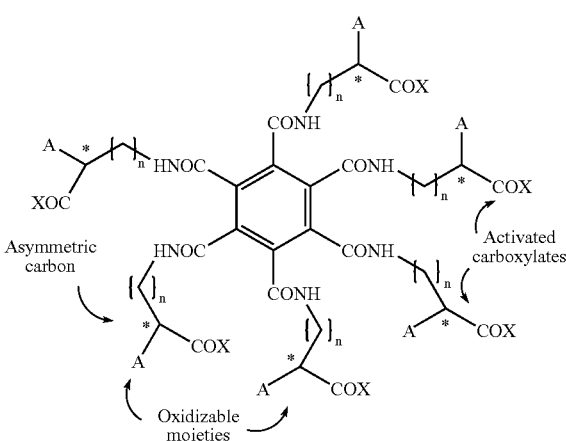

wherein, n is an integer from 0 to 10 and m represents an integer from 0 to 100.

28. A conductive (co)polymer obtained by (co)polymerization of monomers according to claim 1.

29. The conductive (co)polymer according to claim 28, wherein said polymer possessing surface functions.

30. The conductive (co)polymer according to claim 29, wherein said surface functions comprising activated carboxyl groups capable of binding a functional group or a ligand.

31. The conductive (co)polymer according to claim 28, wherein said polymer is combinatorially-designed for desired surface optimization needs.

32. The conductive (co)polymer according to claim 28, wherein same (co)polymer is adsorbed on a microelectrode and capable of binding a ligand.

33. The conductive (co)polymer adsorbed on a microelectrode according to claim 32, wherein said ligand is selected from the group consisting of non-catalytic proteins, enzymes, antibodies and amino-linked RNA, DNA or cDNA.

34. A conductive (co)polymer according to claim 28, wherein same (co)polymer is adsorbed on nanoparticle and capable of binding a ligand.

35. A conductive (co)polymer according to claim 34, wherein same (co)polymer is adsorbed on a magnetic nanoparticle and capable of binding a ligand.

36. A conductive (co)polymer according to claim 28, wherein same (co)polymer is adsorbed on a nanoelectrode in the form of a composite gold-carboxylated conductive (co) polymer.

37. A conductive (co)polymer obtained by electropolymerization of monomers according to claim 1.

38. A conductive (co)polymer obtained by an oxidationl-reduction reaction of monomers according to claim 1.

39. (LL)-Cystine dipyrrole dimethyl ester.

* * * * *